United States Patent [19]

Krystal et al.

[11] Patent Number: 5,626,627
[45] Date of Patent: May 6, 1997

[54] ELECTROCONVULSIVE THERAPY METHOD USING ICTAL EEG DATA AS AN INDICATOR OF ECT SEIZURE ADEQUACY

[75] Inventors: Andrew D. Krystal; Richard D. Weiner, both of Durham, N.C.

[73] Assignee: Duke University, Durham, N.C.

[21] Appl. No.: 508,062

[22] Filed: Jul. 27, 1995

[51] Int. Cl.$^6$ .................................................. A61N 1/32
[52] U.S. Cl. ........................................... 607/45; 128/731
[58] Field of Search .............................. 128/731; 607/45

[56] References Cited

U.S. PATENT DOCUMENTS

| | | | |
|---|---|---|---|
| 4,777,952 | 10/1988 | Pavel | 128/419 |
| 4,870,969 | 10/1989 | Swartz | 128/419 |
| 4,873,981 | 10/1989 | Abrams et al. | 128/419 |
| 4,878,498 | 11/1989 | Abrams et al. | 128/419 |
| 5,269,302 | 12/1993 | Swartz et al. | 128/419 |

OTHER PUBLICATIONS

Andrew D. Krystal et al., "ECT Seizure Therapy Adequacy" *Convulsive Therapy*, vol. 10, No. 2, pp. 153–164 (1994).
Conrad Melton Swartz, "Beyond Seizure Duration as a Measure of Treatment Quality" *Convulsive Therapy*, vol. 9, No. 1, pp. 1–7 (1993).
Nobler et al., "EEG Manifestations during ECT: Effects of Electrode Placement and Stimulus Intensity", *Biol. Psychiatry*, vol. 34, pp. 321–330 (1993).
Andrew D. Krystal et al., "The Largest Lyapunov Exponent of the EEG in EOT Seizures", *Proceedings of the Conference on Measuring Chaos in the Human Brain*, World Scientific Publishing Co. pp. 113–127 (1991).

Krystal et al. "EEG Evidence of More Intense Seizure Activity with Bilateral ECT", *Biol. Psychiatry*, vol. 31, pp. 617–621 (1992).
Krystal et al. "The Effects of ECT Stimulus Dose and Electrode Placement on the ictal Electroencephalogram: An Intraindividual Crossover Study" *Biol Psychiatry*, vol. 34, pp. 759–767 (1993).
Weiner et al., "The Monitoring and Management of Electrically Induced Seizures", *Psychiatric Clinics of North America*, vol. 14, No. 4, (Dec. 1991).
Weiner et al. "EEG Monitoring of ECT Seizures", *The Clinical Science of Electroconvulsive Therapy*, Washington, D.C., American Psychiatric Press, Inc. pp. 93–109, (1993).
Conrad Melton Swartz, "Low–Frequency Ictal EEG Activity and ECT Therapeutic Impact", *Convulsive Therapy*, vol. 9, No. 3, pp. 220–224 (1993).

*Primary Examiner*—William E. Kamm
*Attorney, Agent, or Firm*—Richard E. Jenkins, P.A.

[57] ABSTRACT

A method in electroconvulsive therapy (ECT) to use ictal EEG data for clinical determination of the adequacy of an induced seizure in a patient. The method includes employing an ECT device to apply electricity to the patient in an ECT session to induce seizure activity. The electroencephalographic (EEG) data is detected during the seizure and selected EEG data parameters are derived therefrom. Next, the likely adequacy of the induced seizure is computed by comparing the selected EEG data parameters of the patient to ictal EEG data parameters wherein the adequacy of the corresponding seizure or seizures is known, and the computed likely therapeutic adequacy of the induced seizure is displayed.

23 Claims, 1 Drawing Sheet

ELECTROCONVULSIVE THERAPY METHOD USING ICTAL EEG DATA AS AN INDICATOR OF ECT SEIZURE ADEQUACY

GOVERNMENT INTEREST

This invention was made with Government support under Grant Number 1K20MH-01151 awarded by the National Institutes of Health. The Government has certain rights in the invention.

TECHNICAL FIELD

The present invention relates to electroconvulsive therapy (ECT) and more particularly an improved electroconvulsive therapy (ECT) treatment including methodology for simultaneously and accurately predicting seizure adequacy during treatment.

RELATED ART

Electroconvulsive therapy (ECT) is used to treat certain severe mental disorders such as major depression. At present, as many as 100,000 patients in the U.S.A. receive this treatment yearly and there is evidence that utilization is on the increase. In particular, this internationally used treatment modality is widely recognized on the basis of well-controlled scientific studies as being the most rapid and effective means of producing a clinical remission in episodes of major depressive disorder, a severe, debilitating, and frequently lethal illness which affects millions of Americans during their lifetime. Other such studies have shown ECT to be a relatively safe procedure, with the most widely reported side-effect being memory difficulties, which are nearly always temporary, except that some patients may continue to have difficulty recalling material from around the time period of the ECT treatments. The degree and persistence of these memory difficulties are related to a number of factors, including the extent to which the electrical stimulus intensity exceeds the patient's seizure threshold (as defined below).

In ECT two stimulus electrodes are applied to the patient's scalp. An electric current is applied between these electrodes, only a fraction of which reaches the brain, the rest being deflected by the skin and skull.

The stimulus in ECT is a brief series of electrical square pulses. The width of each pulse, pulse frequency, peak pulse current, and/or overall stimulus duration are adjustable by the physician administering the treatment.

The goal of ECT therapy is the induction of an electrical response in the neural tissue of the patient's brain. This appears on an electroencephalograph (EEG) instrument, using analog printed wavy lines, as a pattern similar to a typical epileptic grand mal seizure pattern. It is believed that the therapeutic benefit of the ECT is primarily due to a series of 4–18 such induced seizures, usually administered at a rate of three times per week.

The specific choice of stimulus parameters is generally tailored to the patient's electrical threshold for inducing this response. This threshold is influenced by factors such as gender, specific type of stimulus electrode location (e.g. stimulation of one side of the head (unilateral (UL) ECT) vs. both sides (bilateral (BL) ECT)), age, and number of prior seizures in the present series. Many physicians now estimate the seizure threshold at the time of the first treatment by using an electrical dose-titration technique that involves the use of increasing levels of stimulus intensity until a desired response is obtained. However, the value of this technique is limited by the fact that seizure threshold rises over the subsequent treatments in the series in a variable and unpredictable manner.

From the very beginnings of ECT the need for some way to assess the adequacy of individual seizures has been apparent. This is the case because there is a delay in time between when a treatment is administered and when the resulting therapeutic benefit and adverse cognitive effects become evident. Thus, there has always been a great need for some way to determine the expected degree of therapeutic response and adverse cognitive effects associated with individual treatments, i.e., to ensure that the induced seizure is "adequate" from the perspective both of therapeutic benefit and side-effects. Such a method for the prediction of the adequacy of the induced seizures would thereby allow ECT practitioners to adjust the treatments administered so that they maximize therapeutic outcome, but do not cause any unnecessary side effects thereby optimizing the administration of this treatment.

The prevailing viewpoint about what constitutes an adequate seizure has evolved since the origin of convulsive therapy. The predominant early view was that seizures were an "all-or-none" phenomenon, such that if a seizure was elicited then therapeutic adequacy was considered to be ensured. Over time the heterogeneity of seizures became apparent. In the early 1960's publications by Ottosson were misinterpreted as implying that the duration of the seizure elicited by ECT was related to the therapeutic effectiveness of the seizure. Bolstered by a 1978 publication by Maletzky, this view developed into the mistaken notion that it was possible to determine seizure adequacy on the basis of the duration of ECT seizures. Since that time a large number of studies have failed to support this conclusion but instead support the view that, while exceeding a seizure duration minimum may be necessary to ensure therapeutic adequacy, it is not sufficient.

More recent evidence suggests that there is a relationship between the beneficial effects and adverse effects associated with ECT treatments and the degree to which the stimulus intensity exceeds the seizure threshold (the amount of electrical charge necessary just barely to cause a seizure). This is termed relative stimulus intensity. Such evidence has suggested that higher relative stimulus intensity was associated with greater cognitive side effects. In addition, higher relative intensity stimuli are associated with a greater therapeutic response rate for one commonly used form of ECT, UL ECT, which is associated with fewer adverse cognitive effects than the other commonly used form of treatment, BL ECT, for which higher relative stimulus intensity is associated with a more rapid response. While this information does not constitute criteria for determining seizure adequacy it at least suggests some potential for being able to predict and thereby to alter therapeutic response and expected side-effects associated with ECT treatments.

Unfortunately, applying these results in the clinical practice of ECT is problematic. Although the use of a seizure threshold titration procedure allows dosing with respect to relative stimulus intensity at the beginning of the treatment course, as noted earlier, ECT treatments induce an uncertain rise in the seizure threshold over the ECT course rendering the relative stimulus intensity unclear. Unfortunately, it is impractical to remedy the situation by performing repeated determinations of the seizure threshold. Nor is the use of a high absolute stimulus intensity to assure the attainment of high relative stimulus intensity viable, since this practice is likely to be associated with unacceptably greater adverse cognitive effects. Thus, recent research highlights the need not only for a marker of the therapeutic potency and adverse effects of ECT seizures but also for the prediction of relative stimulus intensity as this itself would be expected to be associated with therapeutic outcome and the degree of expected adverse effects.

The applicants' invention uses the EEG data, which is routinely recorded noninvasively from the scalp during ECT treatments, for the prediction of ECT seizure adequacy in terms of relative stimulus intensity, therapeutic outcome, and adverse cognitive effects. Prior work with EEG data recorded during and immediately after ECT seizures has not developed models for the determination of seizure adequacy, nor has it provided evidence regarding the clinical utility of ictal EEG data (EEG data recorded during ECT seizures). Thus, such studies leave a lasting need for some scientifically valid way to assess the adequacy of ECT seizures.

The applicants' invention succeeds in meeting this long-felt need by developing ictal EEG models of seizure adequacy that can be implemented in the clinical setting and by demonstrating that these models have a high likelihood of success when implemented for that purpose. This invention is distinguished from prior art in that it is the first actually to develop a method whereby the treatment relative stimulus intensity, expected therapeutic response, and expected cognitive effects associated with an ECT treatment can be determined. Further, it is the first demonstration of a relationship between ECT therapeutic response and computer derived ictal EEG measures. This is particularly important because such computer derived measures can be automated so that accurate and reliable clinical implementation becomes possible. This invention is also the first use of completely automated ictal EEG indices, represents the first implementation of automatic EEG artifact detection and adjustment associated with ECT, and is the first embodiment of a multivariate ictal EEG predictive model.

In the applicants' method, models are developed using data where the treatment relative stimulus intensity, therapeutic potency, and associated adverse effects are known and these models are then used for the prediction of the relative stimulus intensity, expected therapeutic response, and associated side-effects for a given seizure.

While there are prior patents related to ictal EEG data, these patents only pertain to the measurement of seizure duration (see, for example, Somatics, Inc. U.S. Pat. Nos. 4,873,981; 5,269,302; and 4,878,498) and there are no patents known to the applicants relating specifically to seizure adequacy determination. The applicants' invention is a significant advancement in the ECT art by providing a reliable marker of seizure adequacy which has heretofore not been available. As a result, with this invention it will be possible for ECT practitioners to determine the expected beneficial and adverse effects associated with ECT treatments and thereby optimize the effectiveness and safety of this treatment modality.

SUMMARY OF THE INVENTION

The present invention provides a method in electroconvulsive therapy (ECT) to use ictal EEG data for clinical determination of the adequacy of an induced seizure in a patient. The method includes employing an ECT device to apply electricity to the patient in an electroconvulsive therapy session to induce seizure activity. The electrical brain waves (EEG data) of the patient are detected during the seizure and/or immediate post seizure time period and certain selected EEG data parameters are derived therefrom. Next, the likely adequacy of the induced seizure is computed by comparing the selected EEG data parameters of the patient to ictal EEG data parameters wherein the adequacy of the corresponding seizure or seizures is known. Finally, the computed likely therapeutic adequacy of the induced seizure is displayed.

It is therefore an object of the present invention to provide an improved ECT method wherein ictal EEG data is used as a predictor of adequacy of induced seizure activity.

Some of the objects of the invention having been stated hereinabove, other objects will become evident as the description proceeds, when taken in connection with the accompanying drawing as best described hereinbelow.

DETAILED DESCRIPTION OF THE INVENTION

Figure 1:
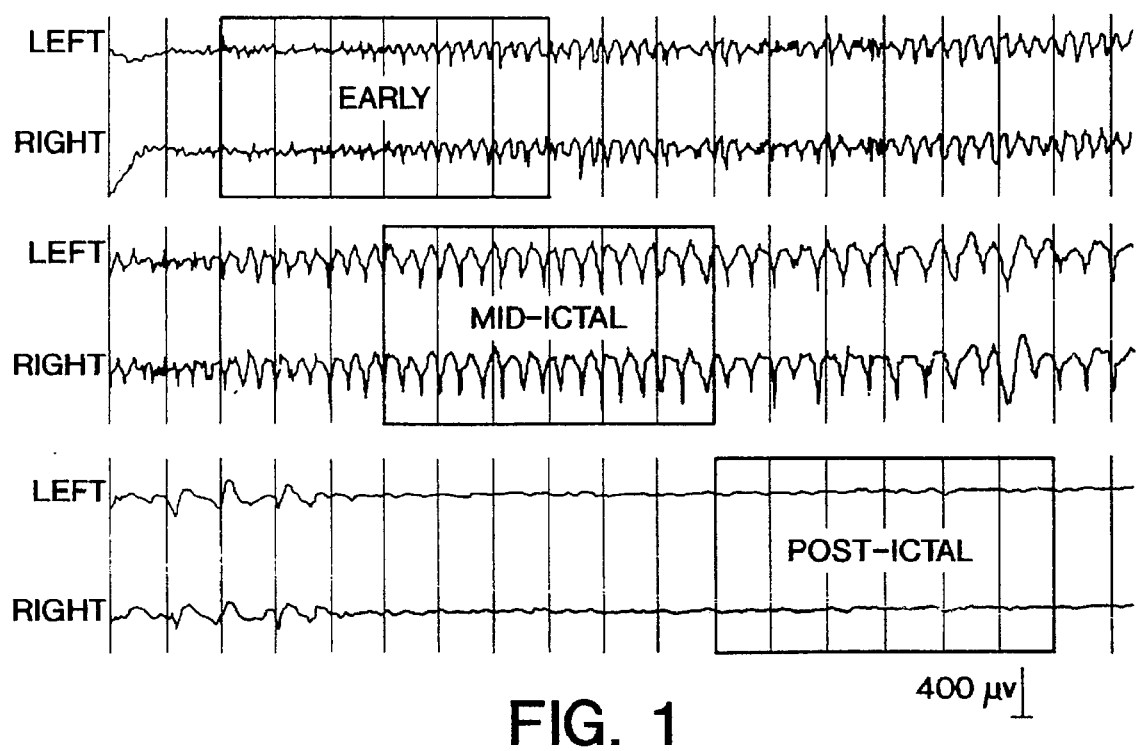
FIG. 1 shows a sample EEG tracing where the segments of data included in the prediction of seizure adequacy are designated.

Applicants now report the development of new ictal EEG models that predict ECT therapeutic adequacy. Applicants have discovered a novel method providing the first use of a multivariate ictal EEG model to predict (1) the adequacy of ECT relative stimulus intensity, (2) therapeutic potency and (3) expected memory side effects associated with ECT treatments. This novel procedure and model represent the discovery of a much-needed clinically applicable marker of the adequacy of individual ECT treatments.

DEVELOPMENT OF MODELS WHICH CHARACTERIZE THE INVENTION

Overview

The development of quantitative multivariate models for ECT seizure adequacy can be thought of as a three stage process: (1) collection of data for model development, (2) computation of ictal EEG variables, and (3) construction and testing of multivariate models for the prediction of stimulus dosing, therapeutic potency, and adverse cognitive effects.

Collection of Data For Model Development

Subjects: Data from twenty-five patients clinically referred for unilateral nondominant ECT were used to assist in the development of the models. All data was collected during the conduction of a research protocol that was independent of the development of this invention. Subjects participating in the protocol all met standardized (DSM-III-R) criteria for major depression (ascertained by a single trained research rater using a structured interview), were strongly right motor dominant on a motor performance test, had not had ECT in the last 3 months, and were without evidence of active cerebral disease. In addition, subjects were free of antidepressant, antipsychotic, and benzodiazepine agents for at least 5 days prior to and during ECT (except for 1 subject who received three nighttime 15-mg doses of temazepam over the ECT course and 3 individuals who had shorter drug-free intervals, respectively, clomipramine 3 days, sertralien 2 days, and trifluoperazine 4 days). In terms of other medications known to affect seizures, one subject received a fixed dosage of theophylline throughout the study. Additional subject characteristics are listed in Table 1.

TABLE 1

Subject Characteristics by Treatment Group

|  | T Group | 2.5T Group |
|---|---|---|
| Men | 2 | 7 |
| Women | 9 | 7 |
| Mean Age | 48.8 | 54.0 |
|  | (14.4) | (10.6) |
| Mean Methohexital Dosage (mg) | 85.4 | 85.8 |
|  | (24.3) | (22.7) |
| Mean Succinylcholine Dosage (mg) | 79.2 | 86.0 |
|  | (17.7) | (19.7) |
| Mean Estimated Seizure Threshold (mC) | 44.3 | 41.1 |
|  | (19.6) | (12.7) |
| Mean Baseline MADRS Score | 38.7 | 36.7 |
|  | (6.4) | (7.4) |
| Mean Seizure Duration (sec) | 73.8 | 66.7 |
|  | (18.7) | (24.0) |

Standard Deviations appear in parentheses

ECT Administration: All patients received bidirectional brief pulse ECT (MECTA SR1 ECT device, manufactured by Mecta Corp. of Lake Oswego, Oreg.) using right UL electrode placement. Routine pharmacologic agents used with ECT included methohexital 1 mg/kg; succinylcholine 1 mg/kg; and 100% of oxygen by mask. Estimation of seizure threshold was accomplished at treatment 1, beginning with a dose of 32 millicoulombs (mC) for females and 48 mC for males. When necessary, restimulation at the same treatment was carried out, using 50% increments, until a seizure of at least 25 seconds EEG duration had been achieved. This resulting final stimulus intensity represented the estimated seizure threshold (T) at the first treatment. Thereafter, patients were randomized to receive a stimulus intensity at subsequent treatments either at T or at a moderately suprathreshold level of 2.5 times estimated seizure threshold (2.5T) intensity for the next 4 treatments (T: N=11 patients; 2.5T: N=14 patients). If a seizure was elicited that was less than 25 seconds in duration, restimulation was delivered at a 50% increment for 2.5T subjects and 25% for individuals assigned to the T condition. Subjects and their treatment teams were both blind to group assignment. Interestingly, applicants discovered that neither seizure threshold nor seizure duration differed between the two groups (see Table 1 above).

EEG Recording: Two channels of EEG were recorded, using a MECTA SR1 ECT device, with left and right prefrontal-to-ipsilateral mastoid derivations and Ag/AgCl electrodes. To ensure a low EEG electrode-scalp impedance, the electrode sites were cleaned with alcohol and an abrasive cleaner (OMNIPREP from D. O. Weaver and Co.), and conduction gel was applied. Simultaneous recordings were made on magnetic tape by using a Vetter Corporation Model C-4 FM tape recorder for subsequent digitization (256 Hz) and analysis by a computer-based EEG acquisition and analysis system (EEGSYS available from Friends of Medical Science, Inc.) and by additional custom software written by applicants.

Therapeutic Outcome Measurement: The Clinical Global Impression Scale (CGI) was used to make a dichotomous therapeutic outcome assessment. The CGI consists of a 7-point severity subscale and a 9-point improvement component. A responder was defined as a subject who achieved at least moderate improvement on the CGI (improvement score <4) and was no more than mildly ill (severity rating ≦3). The CGI was administered by a trained rater: at baseline and 1 day after treatment 5. Baseline Montgomery-Asberg Depression Rating Scale (MADRS) ratings for the two groups appear in Table 1 and were not significantly different.

Memory Function Measurement: The degree of memory impairment associated with the ECT course was assessed via a complex figural memory test which was administered both at baseline and 1 day after treatment 5. Subjects were shown a complex figure and asked to reproduce it immediately and after a period of delay. Because the applicants have previously found that delayed complex figural memory reflected the degree of cognitive impairment associated with ECT, this variable served as the primary measure of memory function. Several test forms were used and their order of administration was counter-balanced.

Statistical analyses: All data were checked for distribution normality and were transformed as indicated to an approximate normal distribution. All measures except coherence data were normalized by a logarithmic transformation. Coherence data were normalized by the Fisher's z transform. The mean treatment number of seizures included in EEG analyses (treatments 2-5 only) did not significantly differ between the two treatment groups (3.38 for T subjects and 3.60 for 2.5T subjects). All analyses were carried out by using the SAS statistical analysis system (available from SAS Institute, Inc.) with two-tailed tests of significance, except for the implementation of adequacy models which were written in the C programming language.

Computation of Ictal EEG Variables

The digitized EEG was split into 3 frequency bands (2-5 Hz, 5.5-13 Hz, and 13.5-30 Hz) by using the fast Fourier transform. Spectral analysis was performed on 6-second (three 2-second epochs) segments of EEG data from the immediate poststimulus (early), midictal, and immediate postictal portions of the seizure (see FIG. 1). For the purposes of computation of ictal EEG variables, in the development of the models, the first 6 artifact-free seconds of data following the ECT stimulus were included in early segment analysis and the first 6 artifact-free seconds of data following seizure termination were utilized in postictal analysis (for model testing, completely automated computation is carried out, see below). The segment for midictal analysis was chosen by a computer program that automatically selected the 6-second portion with the maximum mean peak-to-peak amplitude by testing sequentially overlapping 6-second segments of artifact-free data (epochs 1-3, 2-4, 4-6, etc.). All selection of data segments to be analyzed was done blind to group assignment, treatment number, therapeutic outcome, and degree of cognitive impairment.

For each of these 3 segments, spectral amplitude and interhemispheric coherence were computed for each of the three frequency bands. Coherence was used to reflect the degree of physiologic coupling between the two EEG channels. It is analogous to the interhemispheric correlation of the EEG data in each frequency band. Coherence values varied from 0.0 to 1.0, with a value of 1.0 suggesting a strong linear relationship between the data in the two hemispheres in the frequency band being studied. An additional measure, time to onset of ictal slowing (TSLOW), defined as the first 6-second artifact-free period in which activity in the 2-5 Hz frequency band became greater in amplitude than activity in any other band, was determined through the use of a computer automated procedure.

FIG. 1 is an EEG tracing from a seizure elicited by a 2.5T stimulus. The vertical lines appear at 1 second intervals. The segments of the seizure utilized in ictal EEG analysis appear in the boxes. The ictal EEG parameters associated with this seizure are: Left Early 5.5–13 Hz Amplitude=39.3 μV, Right Early 5.5–13 Hz Amplitude=39.4 μV, Early 2–5 Hz Coherence=0.94, Left TSLOW=4 sec, Right TSLOW=4 sec, Left 2–5 Hz Midictal Amplitude=120 μV, Right 2–5 Hz Midictal Amplitude=127 μV, Left 2–5 Hz Post-ictal Amplitude=8.9 μV, Right 2–5 Hz Post-ictal Amplitude=8.6 μV.

The calculation of all of the ictal EEG indices have been completely automated so that models based on these measures could be implemented in automated fashion in the clinical ECT setting. Early spectral amplitude was automatically calculated from the EEG data recorded in the first 6 seconds post-stimulus and midictal spectral amplitude and TSLOW were automated as described above. Postictal spectral amplitude was automatically computed as the amplitude of the lowest amplitude portion of the seizure excluding the first 6 seconds of the seizure. This allowed postictal amplitude to be determined without the manual determination of the seizure endpoint.

Automation of such ictal EEG models necessitated the automatic detection and adjustment for artifacts that are sometimes present in ictal EEG data, which would otherwise diminish the accuracy of the associated predictors. This was accomplished in several ways. Firstly, the automated computation of postictal amplitude (the amplitude of the lowest amplitude portion of the seizure) decreased the likelihood of artifact contamination in the EEG data utilized in the postictal period, which tend to be higher in amplitude than the EEG signal. Also, the choice of using low frequency mid-ictal amplitude prevents contamination by myogenic artifact, which tends to have higher frequency content.

To provide additional artifact protection, the applicants capitalized on the fact that artifacts cause a predictable effect on each of the EEG variables. All of the spectral amplitude measures are higher in amplitude in the presence of artifact, while TSLOW is made smaller by artifact. As a result, when spectral amplitude measures were below the mean value of the above data set, the influence of spectral amplitude measures on model prediction was doubled by multiplying the Z transformed spectral amplitude variables by 2 (Z transform versions of each variable are used in prediction of seizure adequacy and this transformation involves subtracting off the mean and dividing by the standard deviation of the present data set). Similarly, when TSLOW was greater than the mean of the above data set, the influence of this variable on outcome prediction was doubled. This process diminished the effect of artifact contaminated EEG variables on model performance by weighing more heavily EEG variables which were likely to be free of artifact.

The final set of steps taken to protect against artifact contamination involved the detection of artifact by looking for one of several patterns across 2 or more ictal EEG variables that characterize artifact contamination and subsequently eliminating the effects of variables suspected of being contaminated by artifact. These empirically determined patterns included when early or mid-ictal amplitude were greater than 2 standard-deviations above the mean while post-ictal amplitude was less than the mean of the above described data set. This pattern suggests artifact in the Early or mid-ictal amplitude variable studied. Similarly if TSLOW is 2 standard deviations below the mean and post-ictal amplitude is below the mean, then artifact is suspected in TSLOW. When artifact is suspected in an ictal EEG variable, its Z transformation (the Z transformed version of each variable are used in prediction of seizure adequacy) is set equal to the mean of the Z transformation of all the other ictal EEG variables in the model, that are not suspected of artifact contamination, thereby removing the influence of the artifact on adequacy prediction.

Construction and Testing of Multivariate Models

An Ictal EEG Model for Prediction of ECT Relative Stimulus Intensity: A multivariate logistic regression model was developed and tested for its ability to identify correctly T and 2.5T seizures. The model was developed by using the average of ictal EEG data from treatments 2 and 3 for each subject and was then tested on data from treatments 4 and 5.

To avoid the incorporation of intercorrelated measures, and also to reduce the number of variables in the model, principal components analysis was performed. In this case, the principal components were linear combinations of the original nine EEG variables after z transformation. Although nine potential principal components were generated by the analysis, only those principal components that individually accounted for 10% of more of the variance of the nine (9) ictal EEG variables were utilized. As shown in Table 2 below, the resulting four principal components together accounted for of the variance in the nine EEG variables.

TABLE 2

| First 4 Principal Components of Ictal EEG Variables | | | | |
|---|---|---|---|---|
| | PRIN1 | PRIN2 | PRIN3 | PRIN4 |
| Percentage of Variance Accounted For | 45. | 25. | 13. | 10. |
| Left 5.5–13 Hz Early Amplitude Constant | 0.337023 | 0.145347 | 0.457368 | −0.330347 |
| Right 5.5–13 Hz Early Amplitude Constant | 0.372703 | 0.129997 | 0.387851 | −0.186116 |
| Left 2–5 Hz Midictal Amplitude Constant | 0.416869 | 0.184744 | 0.072316 | 0.387599 |
| Right 2–5 Hz Midictal Amplitude Constant | 0.403066 | 0.164246 | 0.125853 | 0.525657 |
| Left 2–5 Hz Post-Ictal Amplitude Constant | −0.312297 | −0.275883 | 0.505134 | 0.214998 |
| Right 2–5 Hz Post-Ictal Amplitude Constant | −0.28841 | −0.292221 | 0.530298 | 0.259721 |
| Left TSLOW Constant | −0.275992 | 0.515537 | 0.180023 | −0.247008 |
| Right TSLOW Constant | −0.270843 | 0.525611 | 0.192756 | −0.084358 |
| Early 2–5 Hz Coherence Constant | 0.284657 | −0.444206 | 0.114569 | −0.49787 |

Where, for example, PRIN1 would be calculated from the Z transformed data from a given seizure as follows:
PRIN1 = .337023 × Left Early Ampl. + .372703 × Right Early Ampl. + .426869 × Left Mid Ampl. + .403066 × Right Mid Ampl. − .312297 × Left Postictal Ampl. − .28841 × Right Postictal Ampl. − .275992 × Left TSLOW − .270843 × Right TSLOW + .284657 × Early Coherence Each of these four principal components was then entered into a logistic regression model for prediction of stimulus intensity group. Age, but not initial seizure threshold, was included in the model because only the former was found to be a significant covariate. The ability of the model to predict the stimulus intensity group assignment for data from treatments 4 and 5 was then assessed.

Because many ECT practitioners record only one channel of EEG data, reserving the second data channel of most ECT machines for electrocardiographic or electromyographic data, an EEG model of relative stimulus intensity based only on left hemispheric data was also developed and tested (left hemispheric intergroup differences tended to be more significant than for the right hemisphere). This single-channel model was developed by using identical methodology to that described above and included left early 5.5–13-Hz amplitude, left 2–5 Hz midictal amplitude, left 2–5 Hz postictal amplitude, and left TSLOW. The single channel ictal EEG model so developed was also implemented in completely automated form and its associated accuracy in the prediction of ECT seizure relative stimulus intensity adequacy was also tested, and a detailed description of the implementation of this model as it would be carried out in the clinical setting is described.

As outlined above, the first four principal components of the treatment 2–3 means of all nine (9) ictal EEG variables, along with age, were entered into a stepwise logistic regression analysis. Only age and principal components 1 and 4 contributed significantly to the prediction of stimulus intensity group, and therefore principal components 2 and 3 were dropped from the model. Based on the weightings of the two principal components used in the model (1 and 4), the ictal EEG variable that contributed most strongly to the model was midictal 2–5 Hz amplitude, followed by early 5.5–13 Hz amplitude, early 2–5 Hz coherence, postictal 2–5 Hz amplitude, and TSLOW.

This model correctly identified the relative stimulus intensity group for 95% (20/21) of the seizures from the set from which it was developed. This result included a 100% success rate for identifying T seizures (10/10) and a 91% success rate for identifying 2.5T seizures (10/11)—a sensitivity of 100% and specificity of 91% for identifying T seizures. To make a more realistic assessment of the performance of this model, applicants tested it on data from treatments 4 and 5. The resulting overall accuracy of 90% (26/29 correct predictions) included 80% accuracy for identifying T seizures (8/10) and a 95% success rate for identifying 2.5T seizures (18/19)—a sensitivity of 80% and specificity of 95% for identifying T seizures. Testing the model on data for all treatments after treatment 5 yielded a similar predictive accuracy: 88% overall accuracy (35/40); T accuracy 82% (9/11); 2.5T accuracy 904 (26/29).

As described above, a separate model was developed using only data from the left hemisphere. This model was composed of the first and fourth principal components of the four left-side EEG variables (none of the other principal components made a significant contribution) and age (see Table 3). This model correctly predicted the stimulus intensity group of all 22 seizures from which it was developed (100% accuracy) and was only slightly less successful in predicting relative stimulus intensity group than the two-hemisphere model described above when tested on treatment 4 and 5 data. An 88% overall success rate was found (37/42), with a T accuracy of 70% (7/10) and an accuracy of 95% (18/19) in identifying 2.5T seizures.

TABLE 3

Multivariate Logistic Regression Model Coefficients and Significance Level

| Variable | *Regression coefficient (β) | $X^2$ | p Value |
|---|---|---|---|
| PRIN1 | 0.7709 | 7.7 | 0.005 |
| PRIN4 | −0.1880 | 3.9 | 0.05 |
| Age | 4.7875 | 4.1 | 0.04 |
| Constant | −18.3229 | — | — |

*Group membership is predicted for seizure i, as follows:
$G(i) = PRIN1 \times \beta_{PRIN1} + PRIN4 \times \beta_{PRIN4} + Age \times \beta_{Age} + \beta_{Constant}$
Where for the present study $G(i) < 0$ indicated a T seizure and $G(i) > 0$ indicated a 2.5T seizure.
The probability of group membership is: $P(i) = 1/(1 + e^{-G(i)})$
$P(i) < 0.5$ indicates a T seizure and $P(i) > 0.5$ a 2.5T seizure The automated version of the one channel ictal EEG model was associated with an 84% accuracy rate in prediction of the adequacy of ECT seizure relative stimulus intensity on the above described data set and an additional data set including 19 subjects. The parameters of this model differed slightly from those of the model developed for the non-automated EEG indices because postictal amplitude and early amplitude measures differ in the 2 cases.

The detailed steps involved in the calculation of the automated 1 channel UL ECT ictal EEG adequacy model are provided below. As described above, this model includes 4 ictal EEG variables: TSLOW, left 5.5–13 Hz mid-ictal spectral amplitude (LMGB2E), left 2–5 Hz mid-ictal spectral amplitude (LMGB1M), left 2–5 Hz post-ictal spectral amplitude (LMGB1P). The 4 ictal EEG indices listed above were entered into the algorithm below:

(1) Z Transformation of each ictal EEG Variable: The mean of each of the 4 variables as determined in the data set described herein was subtracted from the values obtained from the seizure under study and the difference divided by its standard deviation (determined from the above data set of 25 subjects). This resulted in 4 Z transformed variables: zTSLOW, zLMGB2E, zLMGB1M, zLMGB1P.

(2) Artifact Detection and Adjustment: The 3 Z transformed spectral amplitude variables were multiplied by 2 if their values were below the mean of the above data set (Z transforms <0), and zTSLOW was doubled if it is greater than the mean (zTSLOW >0). The 4 Z transformed variables were also examined for the typical patterns of artifact across these variables and when artifact is suspected, the Z transform of the suspected variable was set equal to the mean of the Z transforms of the remaining artifact-free variables.

(3) Calculation of Principal Components: principal components 1 and 4 of the Z-transformed ictal EEG variables were utilized as predictor EEG variables in this model and calculated as follows: PRIN1=0.63742×zLMB1M +0.53490×zLMB23−0.50420×zLMB1P−0.23099× zTSLOW PRIN4=0.76792×zLMB1M−0.48822×zLMB2E+ 0.35380×zLMB1P+0.21625×zTSLOW (4) Calculation of Probability of Adequacy: Principal Components 1 and 4 were then included along with the natural logarithm of age (ln(Age)) in a logistic regression model (developed from the data collected from the 25 subjects as described above) of the probability (P) of seizure adequacy, where a probability of less than 0.5 indicates an inadequate seizure and a probability of greater than 0.5 is suggestive of adequacy:

$P = 1/(1+e^{-G})$

Where G=1.8786×PRIN1−1.4439×PRIN4+57343×ln(Age) −20.9852

Together, these results prove that attributes of the ictal EEG are likely to be clinically useful as predictors of seizure adequacy. This conclusion is supported in a number of ways.

Strong evidence for the clinical utility of the ictal EEG as a marker of treatment adequacy is the applicants' discovery of an accurate multivariate ictal EEG model for prediction of relative stimulus intensity with UL ECT. This work represents the development of a clinically useful model of UL ECT seizure adequacy. The performance of the model suggests an expected sensitivity and specificity of at least 80%. Only principal components 1 and 4 contributed significantly to the model, suggesting that, among the ictal EEG variables, midictal 2–5 Hz amplitude was the strongest predictor of stimulus intensity group. Although to a lesser extent, the other three types of ictal EEG indices all also contributed to the model and had similar weightings on these two principal components.

An additional model was developed by using ictal EEG data from only the left hemisphere. This model was only slightly less accurate in prediction of group membership than the model including data from both hemispheres. The performance of this model suggests that an ictal EEG algorithm implemented by using only one channel of EEG data will still have a high rate of success in the prediction of adequate relative stimulus intensity. A completely automated version of this model of adequate stimulus intensity was also developed and described in detail. While the applicants developed a number of different automated ictal EEG models of seizure adequacy (see below) and these models were separately developed with both 1 and 2 channel EEG data, and for both UL and BL ECT data), for purposes of brevity and clarity only an automated 1 channel model of UL ECT seizure adequate relative stimulus intensity was described in detail in this application. That this model is associated with an 84% accuracy rate provides the strongest evidence that the models described herein are likely to be successful in the clinical setting for the determination of seizure adequacy. Furthermore, the performance of this single channel model likely underestimates the expected clinical performance of such models since models incorporating other improvements listed elsewhere in this application (the use of 2 channels of data, inclusion of gender, treatment number, etc.) would be expected to perform even better.

An Ictal EEG Model For the Prediction of ECT Therapeutic Outcome: This analysis involved a multivariate ictal EEG logistic regression model of CGI response after treatment 5. The treatment 2–5 means of all ictal EEG variables were entered into this analysis, along with age. Variables that did not significantly contribute to predicting variance in therapeutic response were removed in a stepwise manner. The model was tested by using the "leave-one-out" procedure in which the data for each subject were sequentially removed, a separate logistic regression model was developed with the remaining data, and the resulting model was then tested on the data from the removed subject.

Applicants' results were compatible with a higher therapeutic response rate for 2.5T (70%, 7/10) compared with T (50%, 5/10) ECT. Both right early 5.5–13 Hz ictal EEG amplitude ($X^2$=6.1, P=0.01) and right 2–5 Hz postictal amplitude ($X^2$ =4.9, P=0.03) were significant predictors of therapeutic outcome. There was a trend toward significance for early 2–5 Hz interhemispheric coherence ($X^2$ =4.9, P=0.08). A logistic regression model including these variables and age correctly predicted the therapeutic outcome for 75% (15/20) of the subjects used to develop the model (resubstitution). When the "leave-one-out" technique was employed, the model had a successful prediction rate of 70% (14/20). This result is particularly remarkable given the high degree of "noise" associated with therapeutic response assessments. Because this model differs from that involved in discriminating differences in relative stimulus intensity, it is likely that it will offer additional clinically useful information to ECT practitioners.

An Ictal EEG Model for the Prediction of the Degree of ECT Associated Cognitive Impairment: A multiple regression model of delayed complex figural memory was developed with the average of treatment 2–5 ictal EEG data for all of the 9 ictal EEG parameters described above. Prior to model development, principal components analysis was carried out as described above in the development of the model of relative stimulus intensity. The resulting principal components were entered into a multiple regression model of post-treatment 5 delayed complex figural memory along with age and baseline delayed complex figural memory. Variables that did not significantly contribute to predicting variance in the treatment 5 memory measure were removed in a stepwise manner. Only principal components 6 and 7 made a significant contribution to the prediction of variance in complex figural memory (prin6: partial $R^2$=0.17, F=5.9, p<0.02, prin7: partial $R^2$=0.08, F=3.1, p<0.09) along with baseline figural memory (see Table 4). The overall model accounted for 58% of the variance in complex delayed figural memory ($R^2$=0.58, F=5.4, p<0.006). The derived constants for calculation of principal components 6 and 7 and for the calculation of the predicted degree of memory impairment are specified in Tables 4 and 5 respectively.

TABLE 4

Principal Components 6 and 7 of Ictal EEG Variables.

| Ictal EEG Variable | PRIN6 | PRIN7 |
|---|---|---|
| Left 5.5–13 Hz Early Amplitude Constant | 0.288709 | –0.176692 |
| Right 5.5–13 Hz Early Amplitude Constant | –0.761490 | 0.111034 |
| Left 2–5 Hz Midictal Amplitude Constant | 0.348384 | 0.259564 |
| Right 2–5 Hz Midictal Amplitude Constant | 0.076298 | –0.230679 |
| Left 2–5 Hz Postictal Amplitude Constant | –0.060397 | 0.293882 |
| Right 2–5 Hz Postictal Amplitude Constant | 0.107022 | –0.280419 |
| Left TSLOW Constant | 0.129064 | –0.502627 |
| Right TSLOW Constant | 0.184060 | 0.627113 |
| Early 2–5 Hz Coherence Constant | 0.379407 | 0.157987 |

TABLE 5

Multiple Regression Model Coefficients and Significance level for Prediction of ECT Associated Memory Function

| Variable | *Regression Coefficient ($\beta$) |
|---|---|
| PRIN6 | 7.0184 |
| PRIN7 | 6.5022 |
| Baseline Complex Figural Memory | 0.3565 |
| Constant | 10.9587 |

*The prediction of complex figural memory rating associated with a treatment is as follows:
Predicted Memory = PRIN6 × 7.0184 + PRIN7 × 6.5022 + Baseline Memory × 0.3565 + 10.9587

These results are especially notable since the relationship between ictal EEG variables and memory impairment has never been previously studied. This model is likely to be particularly useful for the clinician because for the first time, it allows a clinical means for assessing the degree of risk of memory dysfunction associated with a particular ECT treatment. In combination with the two previous types of models, this model will allow clinicians to perform a risk to benefit analysis involving the expected degree of side-effects and beneficial effects associated with each ECT treatment, and, thereby optimize the administration of ECT.

Alternative Embodiments of Invention

Applicants have further discovered certain alternative embodiments and additional features of the novel method described herein that are contemplated to be within the scope of the present invention as described and claimed herein. The alternative embodiments and additional features include the following:

(1) An alternative embodiment of this invention that applicants have implemented is to determine the adequacy of an ECT seizure by comparing ictal EEG indices in an individual treatment to the corresponding EEG measures derived from a previous treatment in the treatment course where the adequacy of the associated ECT seizure was known or could be assumed. This approach is particularly powerful because it eliminates ictal EEG variation between individuals, which can be an important factor affecting the accuracy of prediction of ictal EEG models of adequacy. An example of the use of this embodiment which is well suited to present ECT practice is to compare ictal EEG variables at treatment 6 with those at treatment 2 which was administered just after a seizure threshold determination procedure and as a result, the degree to which the treatment 2 stimulus exceeds the seizure threshold is known.

(2) Another alternative embodiment of this invention that applicants have implemented is to develop and apply ictal EEG models for prediction of the adequacy of bilateral (BL) ECT seizures. Such automated ictal EEG models have been developed and tested in a data set of 19 subjects and have been demonstrated to have similar predictive accuracy to the UL ECT models described herein.

(3) Another alternative embodiment of this invention that applicants have implemented is to develop and apply ictal EEG models for the prediction of seizure adequacy taking into account the treatment number of the seizure under study. Applicants have recently obtained data that suggests that earlier treatments, most notably treatment 1, are associated with higher ictal EEG amplitude and smaller immediate postictal amplitude than subsequent treatments. Including the treatment number in ictal EEG models of ECT seizure adequacy resulted in a greater predictive accuracy when treatments earlier in the course were tested, especially treatment 1.

(4) Another alternative embodiment of this invention that applicants have implemented is to develop an ictal EEG model of ECT seizure adequacy including gender as a variable in the model. In developing and testing a model of therapeutic response and adequate relative stimulus intensity with manually derived ictal EEG measures in a set of 40 subjects, applicants found a significant increase in model predictive accuracy when gender was included.

(5) Still another alternative embodiment of this invention is to utilize in an ictal EEG model of ECT seizure adequacy, the high frequency postictal amplitude as an ictal EEG measure. The applicants have recently acquired data suggesting that postictal spectral amplitude in the 13–30 Hz frequency band was a significant predictor of ECT seizure therapeutic potency.

(6) Still another alternative embodiment of this invention is to utilize wavelet analysis in an ictal EEG model of ECT seizure adequacy, to develop an ictal EEG measure. Wavelet analysis allows the frequency content of the EEG data to be reflected over time particularly effectively and is therefore a useful technique for application in an ictal EEG model of adequacy, since evidence presented herein suggests that the frequency content of the ictal EEG plays an important role in such models.

(7) Still another alternative embodiment of this invention is to utilize in an ictal EEG model of ECT seizure adequacy, the time and phase delays between EEG data in 2 EEG channels as an ictal EEG measure. These measures appear to have some promise for differentiating different forms of ECT and therefore may be useful in ictal EEG models of ECT seizure adequacy.

(8) Still another alternative embodiment of this invention is to utilize in an ictal EEG model of ECT seizure adequacy, the correlation between EEG data in 2 EEG leads as an EEG measure. This measure is the time-domain analog of coherence, which was demonstrated herein to be useful for the prediction of seizure adequacy.

(9) Still another alternative embodiment of this invention which applicants have implemented is to utilize in an ictal EEG model of ECT seizure adequacy, the time domain amplitude (where measurements of EEG amplitude are performed in the time domain as opposed to spectral amplitude measures) as an ictal EEG measure. Applicants have also developed models of therapeutic response and relative stimulus intensity on the basis of manually-derived EEG measures obtained in 40 individuals and found that time domain amplitude measurements made significant contributions to those models.

(10) Yet another alternative embodiment of this invention is to utilize in an ictal EEG model of ECT seizure adequacy, the morphologic regularity of the ictal EEG data as an ictal EEG measure. This measure reflects the degree to which the EEG activity takes on a stereotyped or predictable appearance over time. Applicants have implemented both manually-derived and computer versions of this measure and found that they have significantly contributed to models of seizure adequacy.

Applicants have determined that other ictal EEG measurements including largest Lyapunov exponent, signal variance, envelope analysis, and autoregressive models may be used in the practice of the invention described herein.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method in electroconvulsive therapy (ECT) to use ictal EEG data and to compute certain parameters therefrom, wherein the EEG data is obtained from at least one seizure of a known seizure adequacy, for clinical determination of the adequacy of an induced seizure in a patient, the method comprising the steps of:

(a) employing an ECT device to apply electricity, having a stimulus intensity, to the patient in an electroconvulsive therapy session of a course of treatment to induce seizure;

(b) generating EEG data and to compute certain parameters therefrom by detecting the electrical brain waves of the patient during at least one of the seizure and immediate post seizure and selecting the certain EEG data parameters therefrom;

(c) computing a likely therapeutic adequacy of the induced seizure by comparing the selected certain EEG data parameters of the patient to the ictal EEG data parameters of known seizure adequacy; and (d) displaying the computed likely therapeutic adequacy of the induced seizure.

2. A method in electroconvulsive therapy as claimed in claim 1 wherein the therapeutic adequacy of the induced seizure is a degree of the stimulus intensity by which the stimulus intensity exceeds an ictal seizure threshold.

3. A method in electroconvulsive therapy as claimed in claim 1 wherein the therapeutic adequacy of the induced seizure is the therapeutic potency derived from the ictal EEG data parameters obtained from the at least one seizure of a known seizure adequacy.

4. A method in electroconvulsive therapy as claimed in claim 1 wherein the ictal EEG data parameters are used to compute at least one of an expected degree of an associated cognitive dysfunction and an expected degree of an associated cerebral dysfunction, and the adequacy of the induced seizure is at least one of the expected degree of associated cognitive and cerebral dysfunction.

5. A method in electroconvulsive therapy as claimed in claim 1 wherein said step of employing an ECT device comprises securing at least one electrode to the head of the patient and applying electricity through the at least one electrode.

6. A method in electroconvulsive therapy as claimed in claim 1 wherein the selected certain EEG data parameters are selected from the group consisting of TSLOW, coherence, spectral amplitude, largest Lyapunov exponent, time domain amplitude, correlation, signal variance, inter-channel time delay, inter-channel phase difference, envelope analysis, autoregressive models, wavelet analysis, and morphologic regularity.

7. A method in electroconvulsive therapy as claimed in claim 1 wherein the step of computing includes detecting and adjusting the EEG data of the patient to minimize signal artifact effects so as to obtain a more accurate determination of the therapeutic adequacy of the induced seizure.

8. A method in electroconvulsive therapy as claimed in claim 1 wherein the step of computing comprises comparing the selected certain EEG data parameters of the patient to the ictal EEG data parameters of known adequacy, wherein the ictal EEG data parameters are collected from a population of different patients during ECT induced seizures.

9. A method in electroconvulsive therapy as claimed in claim 1 wherein the step of computing comprises comparing the selected certain EEG data parameters of the patient to the ictal EEG data parameters of known adequacy collected from at least one prior ECT induced seizure of the patient during the same treatment course.

10. A method in electroconvulsive therapy as claimed in claim 1 further including developing a predictive model from the ictal EEG data parameters obtained from the at least one seizure of a known adequacy, and wherein, in the step of computing, comparing comprises inputting the selected certain EEG data parameters into the predictive model.

11. A method in electroconvulsive therapy as claimed in claim 10 wherein the predictive model is a multivariate ictal EEG model used for computing likely therapeutic adequacy of the induced seizure and developing the predictive model is accomplished with a multivariate combination of selected ictal EEG data parameters having constants determined by a multivariate regression carried out with the ictal EEG data parameters obtained from the at least one seizure of a known seizure adequacy.

12. A method in electroconvulsive therapy as claimed in claim 1 wherein the step of computing includes tracking changes in a seizure threshold of the patient over the treatment course to compute more accurately the therapeutic adequacy of the induced seizure.

13. A method in electroconvulsive therapy as claimed in claim 1 wherein the step of computing comprises including the patient's age in determining likely therapeutic adequacy of the induced seizure to compute more accurately the therapeutic adequacy of the induced seizure.

14. A method in electroconvulsive therapy as claimed in claim 1 wherein the step of computing comprises including the patient's gender in determining likely therapeutic adequacy of the induced seizure to compute more accurately the therapeutic adequacy of the induced seizure.

15. A method in electroconvulsive therapy as claimed in claim 1 wherein the step of computing comprises including the patient's treatment number in determining likely therapeutic adequacy of the induced seizure to compute more accurately the therapeutic adequacy of the induced seizure.

16. A method in electroconvulsive therapy (ECT) to use ictal EEG data, having certain parameters obtained from at least one seizure of a known adequacy, for clinical determination of the adequacy of an induced seizure in a patient, the method comprising the steps of:

(a) employing an ECT device to apply electricity to the patient in an electroconvulsive therapy session to induce seizure;

(b) generating EEG data, having certain parameters, by detecting the electrical brain waves of the patient during at least one of the seizure and post seizure and selecting the certain EEG data parameters therefrom;

(c) computing a likely therapeutic adequacy of the induced seizure with a multivariate ictal EEG model by comparing the selected certain EEG data parameters of the patient to the ictal EEG data parameters of a known seizure adequacy, wherein the ictal EEG data parameters are collected from a population of different patients during ECT induced seizures; and (d) displaying the computed likely therapeutic adequacy of the induced seizure.

17. A method in electroconvulsive therapy as claimed in claim 16 wherein the selected certain EEG data parameters are selected from the group consisting of TSLOW, coherence, spectral amplitude, largest Lyapunov exponent, time domain amplitude, correlation, signal variance, inter-channel time delay, inter-channel phase difference, envelope analysis, autoregressive models, wavelet analysis, and morphologic regularity.

18. A method in electroconvulsive therapy as claimed in claim 16 further including developing a predictive model from the ictal EEG data parameters obtained from the at least one seizure of a known adequacy and wherein, in the step of computing, comparing comprises inputting the selected certain EEG data parameters into the predictive model.

19. A method in electroconvulsive therapy as claimed in claim 18 wherein the predictive model is a multivariate ictal EEG model used for computing likely adequacy of the induced seizure and developing the predictive model is accomplished with a multivariate combination of selected ictal EEG data parameters having constants determined by a multivariate regression carried out with the ictal EEG data parameters obtained from the at least one seizure of a known seizure adequacy.

20. A method in electroconvulsive therapy (ECT) to use ictal EEG data, having certain parameters obtained from at least one seizure of a known seizure adequacy, for clinical determination of the adequacy of an induced seizure in a patient, the method comprising the steps of:

(a) employing an ECT device to apply electricity to the patient in an electroconvulsive therapy session of a course of treatment to induce a seizure;

(b) generating EEG data, having certain parameters, by detecting the electrical brain waves of the patient during at least one of the seizure and post seizure and selecting the certain EEG data parameters therefrom;

(c) computing a likely therapeutic adequacy of the induced seizure with a multivariate ictal EEG model by comparing the selected certain EEG data parameters of the patient to the ictal EEG data parameters of a known seizure adequacy, wherein the ictal EEG data parameters are collected from one or more prior ECT induced seizures of the patient during the treatment course; and (d) displaying the computed likely therapeutic adequacy of the induced seizure.

21. A method in electroconvulsive therapy as claimed in claim 20 wherein the selected certain EEG data parameters are selected from the group consisting of TSLOW, coherence, spectral amplitude, largest Lyapunov exponent, time domain amplitude, correlation, signal variance, inter-channel time delay, inter-channel phase difference, envelope analysis, autoregressive models, wavelet analysis, and morphologic regularity.

22. A method in electroconvulsive therapy as claimed in claim 20 further including developing a predictive model from the ictal EEG data parameters obtained from the at least one seizure of a known adequacy and wherein, in the step of computing, comparing comprises inputting the selected certain EEG data parameters into the predictive model.

23. A method in electroconvulsive therapy as claimed in claim 22 wherein the predictive model is a multivariate ictal EEG model used for computing likely adequacy of the induced seizure and developing the predictive model is accomplished with a multivariate combination of selected EEG predictor data parameters having constants determined by a multivariate regression carried out with the ictal EEG data parameters obtained from the at least one seizure of a known seizure adequacy.

* * * * *

US005626627C1

(12) EX PARTE REEXAMINATION CERTIFICATE (5064th)
United States Patent
Krystal et al.

(10) Number: US 5,626,627 C1
(45) Certificate Issued: Feb. 22, 2005

(54) ELECTROCONVULSIVE THERAPY METHOD USING ICTAL EEG DATA AS AN INDICATOR OF ECT SEIZURE ADEQUACY

(75) Inventors: Andrew D. Krystal, Durham, NC (US); Richard D. Weiner, Durham, NC (US)

(73) Assignee: Duke University, Durham, NC (US)

Reexamination Request:
No. 90/004,794, Oct. 9, 1997

Reexamination Certificate for:
Patent No.: 5,626,627
Issued: May 6, 1997
Appl. No.: 08/508,062
Filed: Jul. 27, 1995

(51) Int. Cl.[7] ............................................... A61N 1/32
(52) U.S. Cl. ..................................... 607/45; 600/544
(58) Field of Search ........................... 607/45; 600/544, 600/545

(56) References Cited

PUBLICATIONS

Andrew D. Krystal et al., "ECT Seizure Therapy Adequacy", Convulsive Therapy, vol. 10, No. 2, pp. 153–164 (1994).*
Weiner et al., "The Monitoring and Management of Electrically Induced Seizures", Pshychiatric Clinics of Northa America, vol. 14, No. 4, (Dec. 1991).*
Weiner et al., "EEG Monitoring of ECT Seizures", The Clinical Science of Electroconvulsive Therapy, Washington, D.C., American Psychiactric Press, Inc., pp. 93–109 (1993).*
Swartz et al., ECT Instruction Manual, 5th Ed., (Jan. 1994).*
Sackeim et al., "Effects of Stimulus Intensity and Electrode Placement on the Efficacy and Cognitive Effects of Electroconvulsive Therapy", vol. 378, No. 12, pp. 839–845, N.E. Journ Med. (1993).*
Farah et al., "Electroconvulsive Therapy Stimulus Dusing: A Survey of Contemp Practices", vol. 9, No. 2, pp 90–93 (1993).*

* cited by examiner

Primary Examiner—Jeffrey R. Jastrzab

(57) ABSTRACT

A method in electroconvulsive therapy (ECT) to use ictal EEG data for clinical determination of the adequacy of an induced seizure in a patient. The method includes employing an ECT device to apply electricity to the patient in an ECT session to induce seizure activity. The electroencephalographic (EEG) data is detected during the seizure and selected EEG data parameters are derived therefrom. Next, the likely adequacy of the induced seizure is computed by comparing the selected EEG data parameters of the patient to ictal EEG data parameters wherein the adequacy of the corresponding seizure or seizures is known, and the computed likely therapeutic adequacy of the induced seizure is displayed.

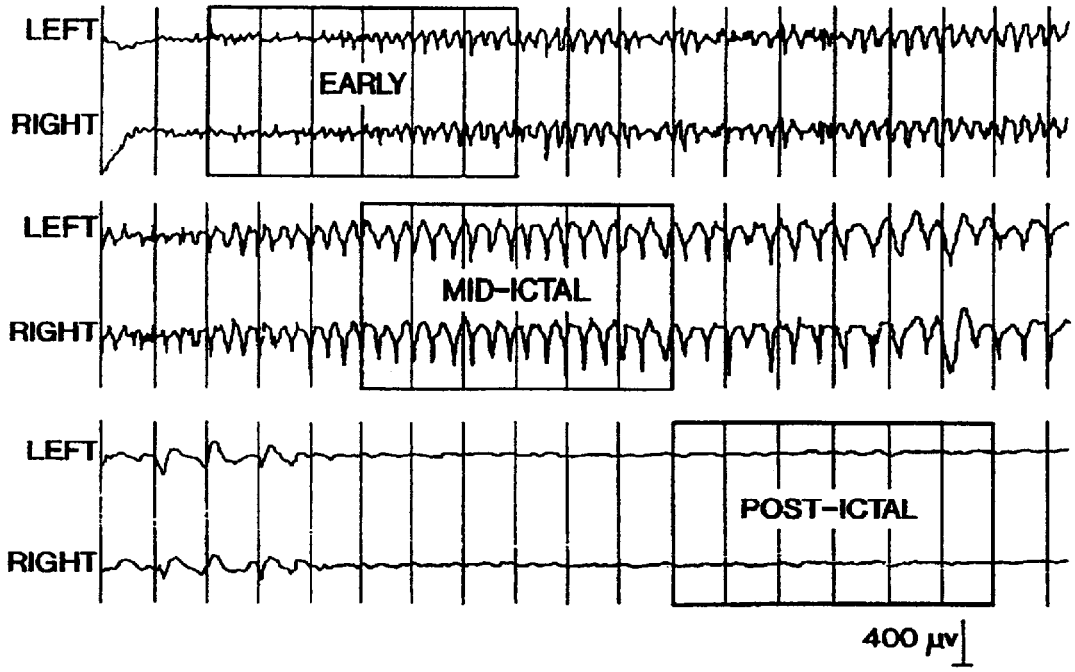

US 5,626,627 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4, 14–16 and 20 are determined to be patentable as amended.

Claims 2, 3, 5–13, 17–19 and 21–23, dependent on an amended claim, are determined to be patentable.

1. A method in electroconvulsive therapy (ECT) to use ictal EEG data and to compute certain parameters therefrom, wherein the EEG data is obtained from at least one seizure of a known seizure adequacy, for clinical determination of the adequacy of an induced seizure in a patient, the method comprising the steps of:
   (a) *obtaining ictal EEG data from at least one seizure of a known seizure adequacy, where adequacy comprises at least one of (1) a therapeutic potency defined in terms of the therapeutic response associated with the treatment, and (2) a treatment associated adverse effect;*
   ([a]*b*) employing an ECT device to apply electricity, having a stimulus intensity, to the patient in an electroconvulsive therapy session of a course of treatment to induce seizure;
   ([b]*c*) generating EEG data and to compute certain parameters therefrom by detecting the electrical brain waves of the patient during at least one of the *induced* seizure and immediate post *induced* seizure and selecting the certain EEG data parameters therefrom;
   ([c]*d*) computing a likely therapeutic adequacy of the induced seizure by comparing the selected certain EEG data parameters of the patient to the ictal EEG data parameters of known seizure adequacy; and
   ([d]*e*) displaying the computed likely therapeutic adequacy of the induced seizure.

4. A method in electroconvulsive therapy [as claimed in claim 1] *(ECT) to use ictal EEG data and to compute certain parameters therefrom, wherein the EEG data is obtained from at least one seizure of a known seizure adequacy, for clinical determination of the adequacy of an induced seizure in a patient, the method comprising the steps of:*
   (a) *employing an ECT device to apply electricity, having a stimulus intensity, to the patient in an electroconvulsive therapy session of a course of treatment to induce seizure;*
   (b) *generating EEG data and to compute certain parameters therefrom by detecting the electrical brain waves of the patient during at least one of the induced seizure and immediate post induced seizure and selecting the certain EEG data parameters therefrom;*
   (c) *computing a likely therapeutic adequacy of the induced seizure by comparing the selected certain EEG data parameters of the patient to the ictal EEG data parameters of known seizure adequacy; and*
   (d) *displaying the computed likely therapeutic adequacy of the induced seizure;*
   wherein the ictal EEG data parameters are used to compute at least one of an expected degree of an associated cognitive dysfunction and an expected degree of an associated cerebral dysfunction, and the adequacy of the induced seizure is at least one of the expected degree of associated cognitive and cerebral dysfunction.

14. A method in electroconvulsive therapy [as claimed in claim 1] *(ECT) to use ictal EEG data and to compute certain parameters therefrom, wherein the EEG data is obtained from at least one seizure of a known seizure adequacy, for clinical determination of the adequacy of an induced seizure in a patient, the method comprising the steps of:*
   (a) *employing an ECT device to apply electricity, having a stimulus intensity, to the patient in an electroconvulsive therapy session of a course of treatment to induce seizure;*
   (b) *generating EEG data and to compute certain parameters therefrom by detecting the electrical brain waves of the patient during at least one of the induced seizure and immediate post induced seizure and selecting the certain EEG data parameters therefrom;*
   (c) *computing a likely therapeutic adequacy of the induced seizure by comparing the selected certain EEG data parameters of the patient to the ictal EEG data parameters of known seizure adequacy; and*
   (d) *displaying the computed likely therapeutic adequacy of the induced seizure;*
   wherein the step of computing comprises including the patient's gender in determining likely therapeutic adequacy of the induced seizure to compute more accurately the therapeutic adequacy of the induced seizure.

15. A method in electroconvulsive therapy [as claimed in claim 1] *(ECT) to use ictal EEG data and to compute certain parameters therefrom, wherein the EEG data is obtained from at least one seizure of a known seizure adequacy, for clinical determination of the adequacy of an induced seizure in a patient, the method comprising the steps of:*
   (a) *employing an ECT device to apply electricity, having a stimulus intensity, to the patient in an electroconvulsive therapy session of a course of a treatment to induce seizure;*
   (b) *generating EEG data and to compute certain parameters therefrom by detecting the electrical brain waves of the patient during at least one of the induced seizure and immediate post induced seizure and selecting the certain EEG data parameters therefrom;*
   (c) *computing a likely therapeutic adequacy of the induced seizure by comparing the selected certain EEG data parameters of the patient to the ictal EEG data parameters of known seizure adequacy; and*
   (d) *displaying the computed likely therapeutic adequacy of the induced seizure;*
   wherein the step of computing comprises including the patient's treatment number in determining likely therapeutic adequacy of the induced seizure to compute more accurately the therapeutic adequacy of the induced seizure.

16. A method in electroconvulsive therapy (ECT) to use ictal EEG data, having certain parameters obtained from at least one seizure of a known adequacy, for clinical determination of the adequacy of an induced seizure in a patient, the method comprising the steps of:

(a) *obtaining ictal EEG data from at least one seizure of a known seizure adequacy, where adequacy comprises at least one of (1) a therapeutic potency defined in terms of the therapeutic response associated with the treatment, and (2) a treatment associated adverse effect;*

([a]*b*) employing an ECT device to apply electricity to the patient in an electroconvulsive therapy session to induce seizure;

([b]*c*) generating EEG data, having certain parameters, by detecting the electrical brain waves of the patient during at least one of the *induced* seizure and post *induced* seizure and selecting the certain EEG data parameters therefrom;

([c]*d*) computing a likely therapeutic adequacy of the induced seizure with a multivariate ictal EEG model by comparing the selected certain EEG data parameters of a known seizure adequacy, wherein the ictal EEG data parameters are collected from a population of different patients during ECT induced seizures; and ([d]*e*) displaying the computed likely therapeutic adequacy of the induced seizure.

20. A method in electroconvulsive therapy (ECT) to use ictal EEG data, having certain parameters obtained from at least one seizure of a known seizure adequacy, for clinical determination of the adequacy of an induced seizure in a patient, the method comprising the steps of:

(a) *obtaining ictal EEG data from at least one seizure of a known seizure adequacy, where adequacy comprises at least one of (1) a therapeutic potency defined in terms of the therapeutic response associated with the treatment, and (2) a treatment associated adverse effect;*

([a]*b*) employing an ECT device to apply electricity to the patient in an electroconvulsive therapy session of a course treatment to induce seizure;

([b]*c*) generating EEG data, having certain parameters, by detecting the electrical brain waves of the patient during at least one of the *induced* seizure and post *induced* seizure and selecting the certain EEG data parameters therefrom;

([c]*d*) computing a likely therapeutic adequacy of the induced seizure with a multivariate ictal EEG model by comparing the selected certain EEG data parameters of a known seizure adequacy, wherein the ictal EEG data parameters are collected from one or more prior ECT induced seizures of the patient during the treatment course; and ([d]*e*) displaying the computed likely therapeutic adequacy of the induced seizure.

\* \* \* \* \*